United States Patent
Steinhauser et al.

(10) Patent No.: US 9,967,961 B2
(45) Date of Patent: May 8, 2018

(54) SIMULATED SPATIAL LIVE VIEWING OF AN OBJECT FROM VARIABLE VIEW-POINTS

(71) Applicant: KONINKLIJKE PHILIPS N.V., Eindhoven (NL)

(72) Inventors: Heidrun Steinhauser, Eindhoven (NL); Michiel Wouter De Wildt, Den Bosch (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 161 days.

(21) Appl. No.: 14/383,268

(22) PCT Filed: Mar. 19, 2013

(86) PCT No.: PCT/IB2013/052158
§ 371 (c)(1),
(2) Date: Sep. 5, 2014

(87) PCT Pub. No.: WO2013/144771
PCT Pub. Date: Oct. 3, 2013

(65) Prior Publication Data
US 2015/0043714 A1    Feb. 12, 2015

Related U.S. Application Data

(60) Provisional application No. 61/615,414, filed on Mar. 26, 2012.

(51) Int. Cl.
*H01J 35/30* (2006.01)
*H05G 1/30* (2006.01)
(Continued)

(52) U.S. Cl.
CPC ............ *H05G 1/30* (2013.01); *A61B 6/022* (2013.01); *A61B 6/4028* (2013.01);
(Continued)

(58) Field of Classification Search
CPC ........ A61B 6/00; H01J 35/00; H01J 2235/00; H05G 23/00; H05G 2223/00
See application file for complete search history.

(56) References Cited

U.S. PATENT DOCUMENTS 3,432,658 A    3/1969  Quinn
4,383,328 A *  5/1983  Kurihara ............. G03B 42/02
                                              378/42
(Continued)

FOREIGN PATENT DOCUMENTS

DE    102010012394 A1    9/2011
WO       2005093663 A1   10/2005
(Continued)

*Primary Examiner* — Thomas R Artman
(74) *Attorney, Agent, or Firm* — Larry Liberchuk (57) ABSTRACT

A system for providing a simulated spatial live viewing of an object includes a cathode arrangement configured to generate an electron beam towards a target area of an anode, and a processor configured to control the electron beam to hit the anode at a moving focal spot that moves at least in a first moving direction transverse to a viewing direction. Thus, X-ray radiation is generated by the electron beam impinging on the moving focal spot. Further, the system includes a detector configured to detect X-ray radiation at least partially passing an object and to generate respective X-ray detection signals. The processor is further configured to generate monoscopic 2D images based on the detection signals, where the monoscopic 2D images relate to different view-points as defined by the moving focal spot. A display is configured to display the monoscopic 2D images are from the different view-points.

17 Claims, 7 Drawing Sheets

(51) Int. Cl.
  *A61B 6/02* (2006.01)
  *A61B 6/00* (2006.01)
  *G01N 23/04* (2018.01)
  *H01J 35/14* (2006.01)

(52) U.S. Cl.
  CPC ............ *G01N 23/046* (2013.01); *H01J 35/14* (2013.01); *H01J 35/30* (2013.01); *H01J 2235/086* (2013.01)

(56) References Cited

U.S. PATENT DOCUMENTS

| | | | |
|---|---|---|---|
| 4,926,452 A | 5/1990 | Baker | |
| 5,097,492 A | 3/1992 | Baker | |
| 5,615,279 A * | 3/1997 | Yoshioka | G06T 11/005 378/7 |
| 5,625,661 A | 4/1997 | Oikawa | |
| 5,682,412 A | 10/1997 | Skillicorn et al. | |
| 6,907,110 B2 * | 6/2005 | Apel | H01J 35/08 378/10 |
| 7,940,886 B2 | 5/2011 | Kuzmanovic | |
| 7,974,450 B2 | 7/2011 | Ritter | |
| 8,520,803 B2 * | 8/2013 | Behling | H01J 35/10 378/124 |
| 9,418,816 B2 * | 8/2016 | Kondo | A61B 6/032 |
| 9,427,198 B2 * | 8/2016 | Steinhauser | A61B 6/022 |
| 9,554,757 B2 * | 1/2017 | Steinhauser | H01J 35/30 |
| 2002/0126796 A1 * | 9/2002 | Yamasaki | A61B 6/022 378/42 |
| 2003/0002627 A1 | 1/2003 | Espinosa | |
| 2008/0009715 A1 | 1/2008 | Kukuk et al. | |
| 2008/0080662 A1 * | 4/2008 | Shukla | A61B 6/032 378/4 |
| 2010/0040196 A1 | 2/2010 | Zhang et al. | |
| 2010/0080357 A1 * | 4/2010 | Katcha | H01J 35/10 378/124 |
| 2010/0329534 A1 | 12/2010 | Biermann et al. | |
| 2011/0002442 A1 | 1/2011 | Thran | |
| 2012/0082300 A1 | 4/2012 | Onken | |
| 2015/0043714 A1 * | 2/2015 | Steinhauser | A61B 6/022 378/62 |
| 2015/0071404 A1 * | 3/2015 | Steinhauser | H01J 35/30 378/41 |

FOREIGN PATENT DOCUMENTS

| | | |
|---|---|---|
| WO | 2010146504 A1 | 12/2010 |
| WO | 2012123843 A1 | 9/2012 |

* cited by examiner

SIMULATED SPATIAL LIVE VIEWING OF AN OBJECT FROM VARIABLE VIEW-POINTS

CROSS REFERENCE TO RELATED APPLICATIONS

This application is a national filing of PCT application Serial No. PCT/IB2013/052158, filed Mar. 19, 2013, published as WO 2013/144771 A2 on Oct. 3, 2013, which claims the benefit of U.S. provisional application Ser. No. 61/615,414 filed Mar. 26, 2012, which is incorporated herein by reference.

FIELD OF THE INVENTION

The present invention relates to an X-ray tube for simulated spatial live viewing of an object, an X-ray imaging system for simulated spatial live viewing of an object, a method for providing spatial live viewing of an object, and a computer program element as well as a computer readable medium.

BACKGROUND OF THE INVENTION

In medical imaging, the provision of spatial information is helpful for understanding the current situation, for example when examining an object, for example a patient. In X-ray imaging, stereoscopic viewing as a way of providing spatial viewing is provided for live 3D stereo viewing of the object. For example, WO 2010/146504 A1 describes an X-ray tube for generating two focal spots, thus providing stereo images. To provide the so-to-speak two different images to the user, i.e. in form of a right and a left image, specific 3D displays are used, or 3D glasses that have to be used by, for example, the surgeon. However, the 3D display requires a predetermined distance between the display and the user watching the display, which means practical moving restrictions for the surgeon. Further, with respect to 3D glasses, the user must wear, or at least activate these glasses, for example when having synchronized shutter mechanisms.

SUMMARY OF THE INVENTION

Thus, there is a need to provide spatial (live depth) information to the user with reduced requirements concerning to maintain a particular position, e.g. with respect to a 3D display, or to wear or activate additional components, such as 3D glasses or 3D display.

The object of the present invention is solved by the subject-matter of the independent claims, wherein further embodiments are incorporated in the dependent claims.

It should be noted that the following described aspects of the invention apply also for the X-ray tube for simulated spatial live viewing of an object, the X-ray imaging system for simulated spatial live viewing of an object, the method for providing spatial live viewing of an object, the computer program element and the computer readable medium.

According to a first aspect of the present invention, an X-ray tube for simulated spatial live viewing of an object is provided, comprising a cathode arrangement, an anode, and control means. The cathode arrangement and the anode are provided to generate an electron beam from the cathode arrangement towards a target area of the anode to generate X-ray radiation by electrons impinging on the target area. The control means are configured to control the electron beam such that the electrons hit the anode at a moving focal spot. The control means are further configured to provide a movement of the focal spot at least in a first moving direction transverse to a viewing direction.

According to an exemplary embodiment, X-ray imaging is provided with a gradually moving focal spot.

According to a further exemplary embodiment, the control means are configured to provide a movement of the focal spot at least also in a second moving direction, which is transverse to the first moving direction and transverse to the viewing direction.

According to an exemplary embodiment, the cathode arrangement comprises a single cathode and the control means are deflection means provided to deflect the electron beam.

According to a further exemplary embodiment, the cathode arrangement comprises a plurality of Carbon Nanotube emitters, which Carbon Nanotube emitters are configured to provide an electron beam with a moving focal spot position. The control means are provided as a control arrangement of the Carbon Nanotube emitters.

The term spatial live viewing relates to providing spatial information as if, for example, stereoscopic viewing is applied.

According to a second aspect of the present invention, an X-ray imaging system for simulated spatial live viewing of an object is provided, comprising an X-ray source, an X-ray detector, a processing unit, and a display device. The X-ray source is an X-ray tube according to one of the above-mentioned examples. The X-ray detector is configured to provide X-ray detection signals to the processing unit. The processing unit is configured to generate monoscopic 2D images based on the detection signals, which monoscopic 2D images relate to different view-points as defined by the moving focal spot. The display device is a 2D display configured to show the monoscopic X-ray images from the different view-points.

According to an exemplary embodiment, the processing unit is configured to compute a moving average of several images from different moving focal spots. The moving average is provided for a predetermined period of time.

According to a third aspect of the present invention, a method for providing spatial live viewing of an object is provided, comprising the following steps:

a) generating an electron beam from a cathode arrangement towards a target area of an anode and controlling the electron beam such that the electron beam hits the anode at a moving focal spot; the electron beam is controlled such that the focal spot moves at least in a first moving direction transverse to a viewing direction;

b) generating X-ray radiation by the electron beam impinging on the moving focal spot;

c) detecting X-ray radiation at least partially passing an object and generating respective X-ray detection signals;

d) generating monoscopic 2D images based on the detection signals, which monoscopic 2D images relate to different view-points as defined by the moving focal spot;

e) displaying the monoscopic X-ray images from the different view-points.

According to an exemplary embodiment, in step e), live image data of the object is continuously shown for the moving view-points providing spatial impression about the object.

According to an exemplary embodiment, in step b), the focal spot is moved along a loop-like movement path.

According to an aspect of the present invention, X-ray focal spot movements during X-ray imaging provides live depth information/sensation by the movement size of various objects. The resulting motion trajectories can give the physician live depth information on a 2D display. For example, knowing that the detector and, for example, the patient stay fixed and that only the X-ray spot is moving, this helps to perceive the depth information in an intuitive way. Objects which are near to the detector stay fixed. The farther away an object is from the detector, the larger is the movement. Thus, when arranging the detector towards a physician, and the X-ray source away from the physician, the user is provided with depth information in an intuitive way. According to a further aspect, it is also possible to place the X-ray detector below the patient and the X-ray tube above the patient. This way, the X-ray images look like resulting from head movements of the physician. Similar would be the case also for the opposite arrangement, when the detector is arranged towards the physician, e.g. above the patient table. According to an aspect of the present invention, spatial information is provided without the requirements for a special 3D display or 3D glasses. A further advantage lies in the fact that it is possible to provide the spatial information in a way that does not require the physician to accommodate to 3D information, as is the case every time when looking from the patient to a 3D display and vice versa. Rather, according to the present invention, a 2D image is provided where the spatial information is provided by watching a sequence of the images, namely due to the moving focal spot. Thus, the images that are shown according to the present invention are not real "stereo images", but rather 2D images, which contain and show the spatial information over time. Thus, the term "simulated stereoscopic live viewing" may be used. Further, all physicians (and staff) are able to see the spatial information, without the need for all personnel to wear 3D glasses. According to the present invention, the movement of the focal spot results in different moving ratio of elements in dependency from their spatial arrangement within the object. As indicated above, objects closer to the X-ray source appear different than objects in a larger distance to the X-ray source. It is noted that the term "object" relates to features or other visible characteristics of certain regions or locations of the "object", i.e. of the patient, as an example. 2D images give clear information about x and y position of an object. But the z (depth) position is ambiguous. X-ray images are absorption images: depth clues like occlusion are missing. Presenting images from variable view-points gives the physician depth information/sensation by the relative movement size (or amount of blurring) of the displayed object of interest with respect to other displayed objects (parts).

These and other aspects of the invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
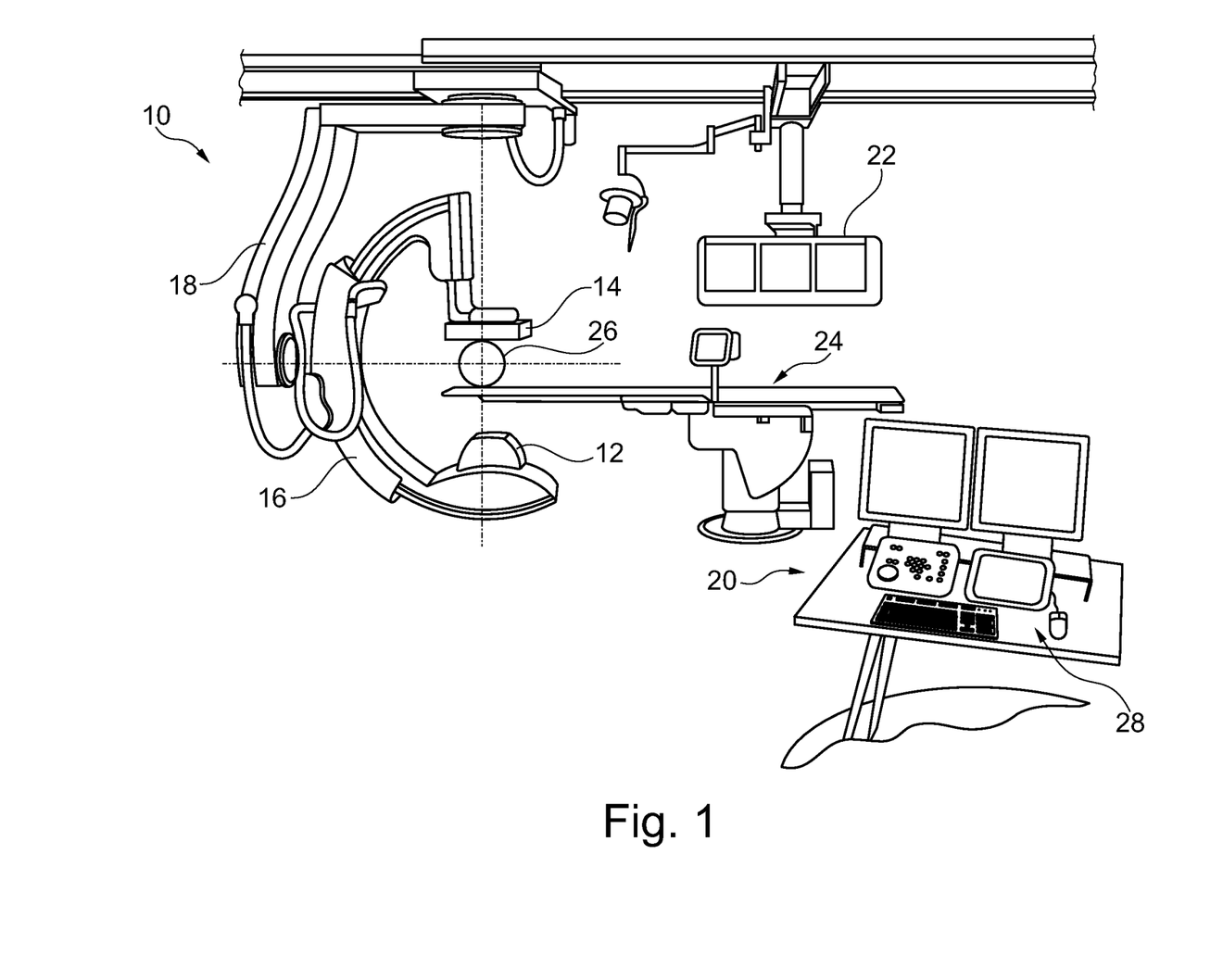
FIG. 1 schematically shows an X-ray imaging system according to the present invention.

FIG. 1 shows an X-ray imaging system 10 for simulated spatial live viewing of an object. The X-ray imaging system 10 is shown as a so-called C-arm arrangement, where an X-ray source 12 and an X-ray detector 14 are provided on opposing ends of a C-arm structure 16, which is movably supported by a ceiling support 18. Further, a processing unit 20 is shown together with a display device 22. Further, a support 24 for supporting an object 26 is shown, for example a patient support table supporting a patient.

Still further, an interface arrangement 28 together with some monitors is shown in relation with the processing unit 20 (not further shown). The X-ray source is an X-ray tube 30, which will be described in more detail in the following figures. The X-ray detector is configured to provide X-ray detection signals to the processing unit 20. The processing unit 20 is configured to generated monoscopic 2D images based on the detection signals, which monoscopic 2D images relate to different view-points as defined by the moving focal spot. The display device 22 is a 2D display configured to show the monoscopic X-ray images from the different view-points.

Figure 2:
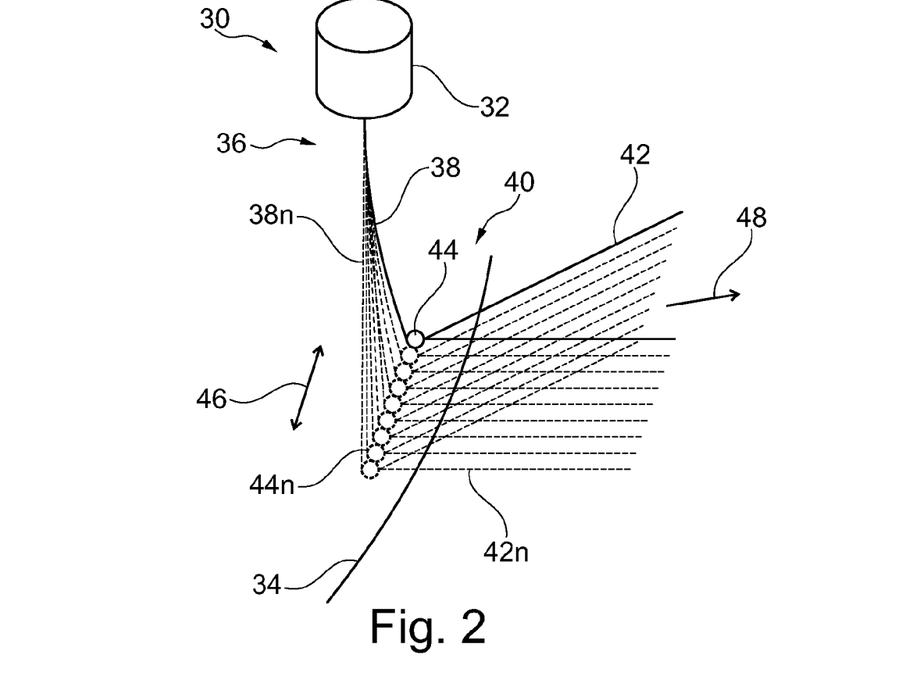
FIG. 2 shows an exemplary embodiment of an X-ray tube in a simplified illustration according to the present invention.

FIG. 2 shows an example of the X-ray tube 30 for simulated spatial live viewing of an object. The X-ray tube 30 comprises a cathode arrangement 32, an anode 34, and control means 36 that are not further shown in FIG. 2. The cathode arrangement 32 and the anode 34 are provided to generate an electron beam 38 from the cathode arrangement 32 towards a target area 40 of the anode 34 to generate X-ray radiation 42 by electrons impinging on the target area 40. The control means 36 are configured to control the electron beam such that the electrons hit the anode 34 at a moving focal spot 44. The control means are further configured to provide a movement of the focal spot at least in a first moving direction 46 transverse to a viewing direction 48.

As indicated with dotted lines 38n, the electron beam is controlled, e.g. deflected, towards different focal spot positions 44n, indicated with dotted circles. Thus, as a result, different X-ray beams 42n are provided, which are also shown in a dotted, respectively dashed line type. In other words, X-ray imaging is provided from a number of focal spots along a movement path. According to the present invention, X-ray imaging is provided with a gradually moving focal spot. As a result, the image shown as a live image is constantly changing in direct dependency from the movement of the focal spot.

Thus, the user watching the provided X-ray image is provided with an impression of the spatial (live depth) information by combining the presented 2D image sequence. In other words, a spatial or stereoscopic viewing is so-to-speak simulated. The simulated spatial or stereoscopic viewing may also be referred to as simulated 3D viewing, 2D depth viewing or 2D-plus viewing. The simulated stereoscopic viewing may also be referred to as perceived stereoscopic viewing.

Figure 3:
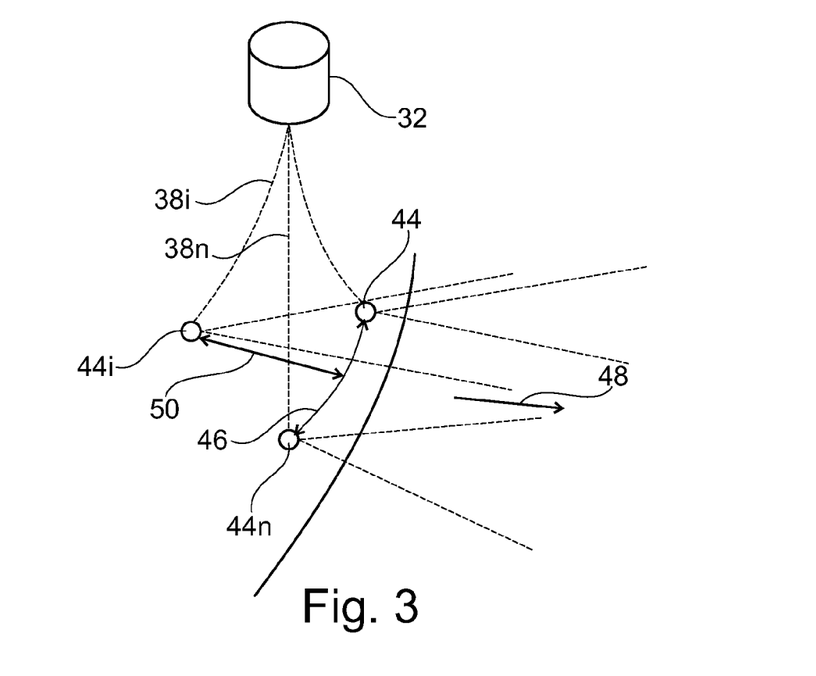
FIG. 3 shows a further exemplary embodiment of an X-ray tube according to the present invention.

FIG. 3 shows a further example, where the control means are configured to provide a movement of the focal spot at least also in a second moving direction 50, which is transverse to the first moving direction 46 and transverse to the viewing direction 48. The resulting focal spot positions are indicated with only one exemplary position, indicated with reference numeral 44a. Of course, also a plurality of positions is possible, for example also by combining the first and the second movement.

The first moving direction may also be referred to as first stereo-direction, and the second moving direction may be referred to as second stereo-direction. The first stereo-direction is also referred to as horizontal direction and the second stereo-direction is referred to as vertical direction, which will be explained further below, for example in relation with FIGS. 6, 7, and FIGS. 8, 9.

Figure 4:
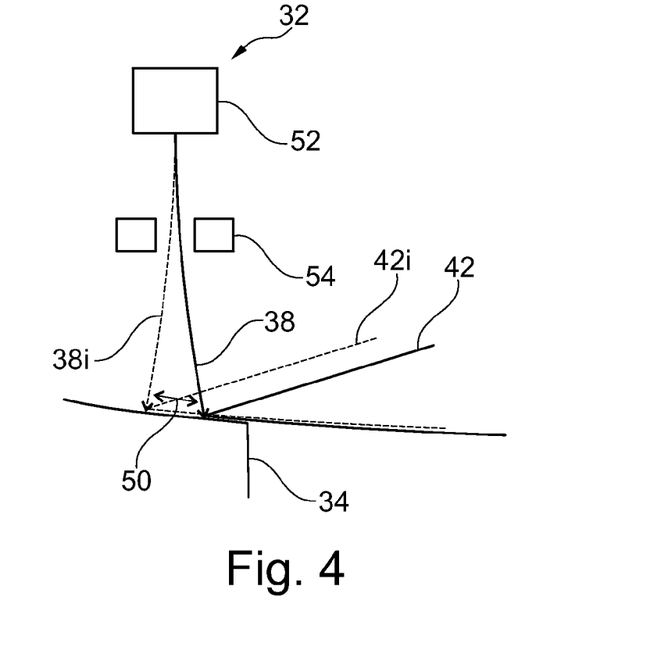
FIG. 4 shows a further exemplary embodiment of an X-ray tube according to the present invention.

FIG. 4 shows an example, wherein the cathode arrangement 32 comprises a single cathode 52, and the control means are deflection means 54, provided to deflect the electron beam. For example, the deflection is provided electrostatically or electromagnetically. Thus, moving focal spot positions are provided.

Figure 5:
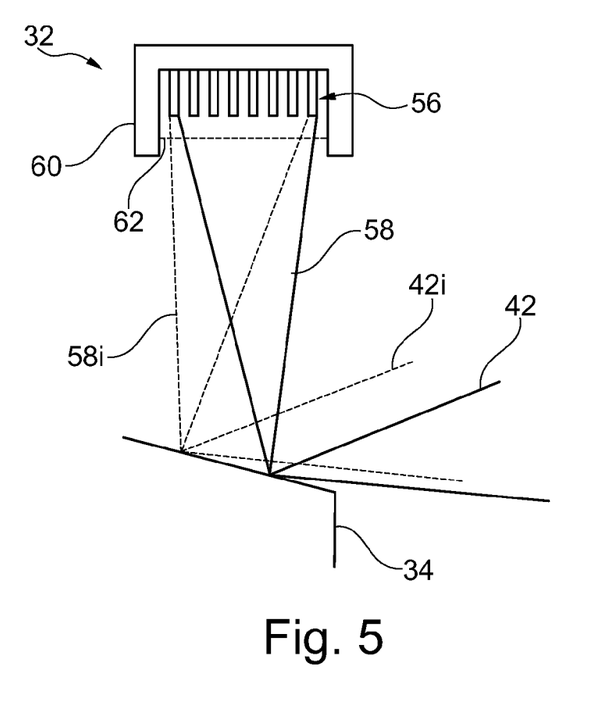
FIG. 5 shows a still further exemplary embodiment of an X-ray tube according to the present invention.

FIG. 5 shows a further exemplary embodiment, wherein the cathode arrangement 32 comprises a plurality of Carbon Nanotube emitters 56, which are configured to provide an electron beam 58 with moving focal spot positions. As an example only, a second shape/direction of the electron beam is indicated with dotted lines and reference numeral 58a. Of course, other shapes/directions are also provided. The Carbon Nanotube emitters 56 may be provided with steering or guiding electrodes 60 and a gate structure 62 to control the Carbon Nanotube emitters such that different target spots or target areas can be hit by the respective electron beam in order to generate different X-ray radiation 42, 42i. In another embodiment, a plurality of steerable cathodes is provided, instead of one steerable cathode as in FIG. 5, to create a moving X-ray source (focal spot).

Figures 6, 7:
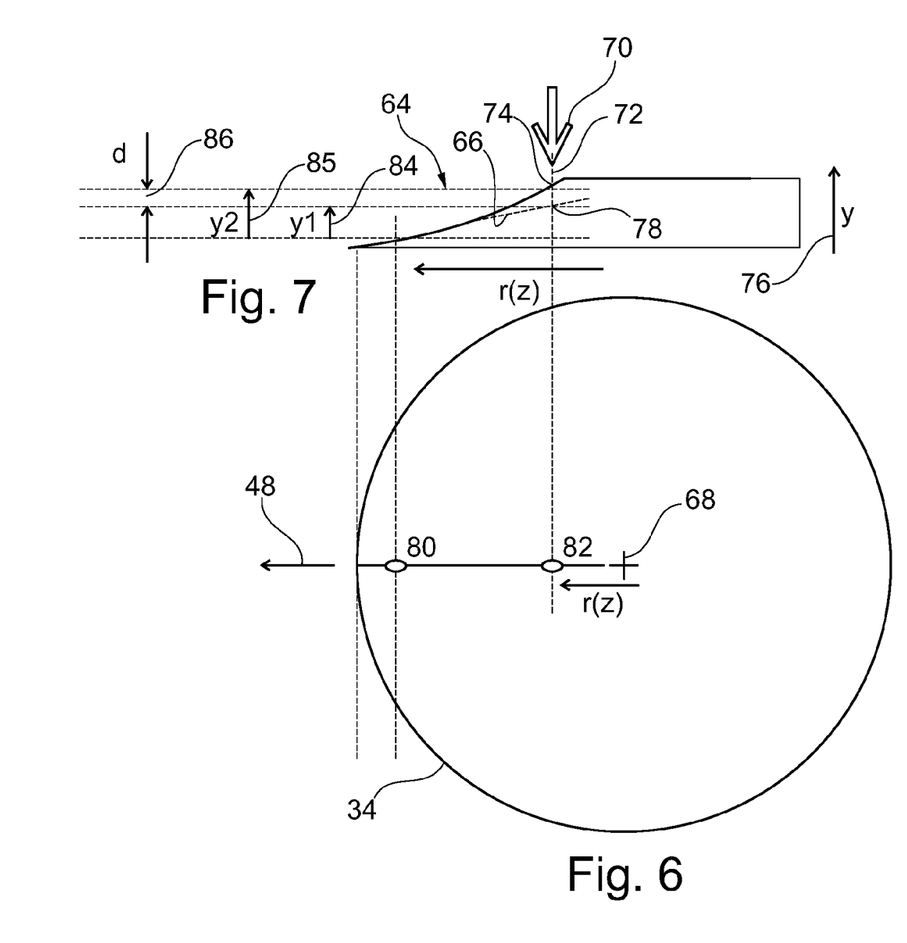
FIG. 6 shows a further exemplary embodiment of an X-ray tube according to the present invention in a top view of focal spots arranged on a rotating anode.
FIG. 7 shows a cross-section of the X-ray tube of FIG. 6.

FIGS. 6 and 7 show a further example, wherein the anode 34 is provided as a rotating anode disk. FIG. 6 shows a top view with an arrangement of different focal spot positions, and FIG. 7 shows a cross-section. The anode 34 is provided with an inclined focal track area 64 providing different heights for the focal spot positions. As can be seen, the focal track area 64 is provided with an increasing inclination degree. Instead of having an inclined surface with a continuous degree of inclination, i.e. the same angle throughout the surface, as indicated with a dotted line 66, the surface is, when starting at the outer edge and moving towards the inner part in direction of a rotating axis 68, the surface is moving away from the dotted line 66, thus representing an increasing inclination degree. An electron beam is indicated with an arrow 70, hitting the anode surface. At the intersection of the dotted line representing the electron beam, which dotted line is indicated with reference numeral 72, and the surface of the anode, which intersection is indicated with reference numeral 74, is the height of the focal spot position, namely the height of the point 74, wherein the height is referring to a y-direction 76 which is aligned parallel to the rotating axis 68 and thus perpendicular to the viewing direction 48, which is also referred to as r-direction. For comparison, also an intersection 78 of the electron beam direction 72 and the dotted line 66 is marked, which would represent the focal spot's height in case of a continuous inclination degree. By projecting the dotted lines onto the top view of FIG. 6, the following becomes visible. A first mark 80 represents a first focal spot position on the so-to-speak lower portion of the focal track area 64. A second mark 82 represents the position of a second focal spot in order to achieve the height of the intersection point 78. A first arrow 84 represents the height that would be achieved in case of a continuous inclination degree. A second arrow 85 represents the height that is achieved due to the increasing inclination degree. Thus, the increasing inclination degree provides a delta 86 plus in height without any further extension in r-direction. In other words, compared with a continuous, i.e. linear inclination profile, the increasing inclination degree provides a reduced radial extension of the focal track for providing similar focal spot heights (y-movement or y-deflections).

It must be noted that the aspects of FIGS. 6 and 7, and also the features mentioned and explained in relation with FIGS. 8 to 11 are described in relation with the feature of the anode being a rotating anode disk. However, it is also provided to have a non-rotating anode disk with similar features. In addition, it is also noted that also the features in the previous figures, e.g. FIGS. 2 to 5, can be combined with the rotating anode disk, although not explicitly shown.

Figures 8, 9:
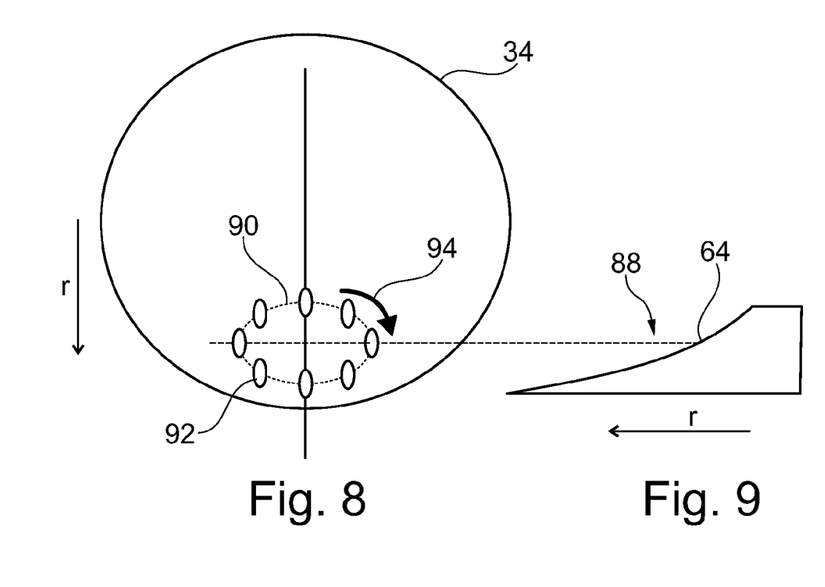
FIG. 8 shows a further example of an X-ray tube in a top view plan.
FIG. 9 shows a cross-section of FIG. 8.

According to a further example, as shown in FIGS. 8 and 9, the anode is a rotating anode disk with an edge portion 88 having a truncated cross-section with the increasing inclination degree, i.e. the inclined focal track area 64. The focal spot is provided on a focal track arranged on the edge portion.

For example, the focal spot is moved along a loop-like movement path 90, as shown in FIG. 8, for which a number of focal spot positions 92 is shown. However, also other movement paths can be provided, such as a swivelling movement, or a straight line movement path, and of course all other geometric compositions. It is further noted that FIG. 8 shows only some of the plurality of focal spot positions for better visibility. Of course, also intermediate positions can be provided. An arrow 94 indicates the loop-like continuous movement of the focal spot along the movement path 90.

FIG. 8 shows the top view of the focal spots on the anode surface, and FIG. 9 shows a cross-section.

Figure 10:
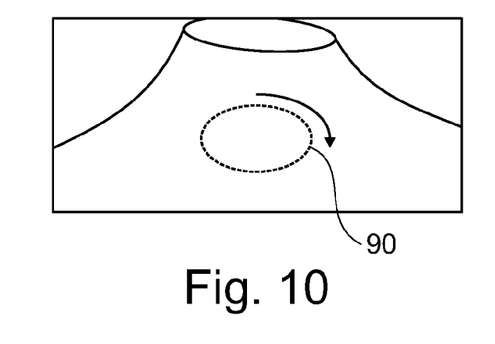
FIG. 10 schematically illustrates a further X-ray tube in a perspective view.

FIG. 10 shows a perspective view with the loop-like movement path 90 projected onto a truncated cross-section of the surface.

Figure 11:
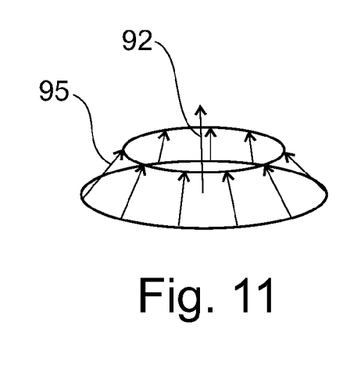
FIG. 11 shows a further exemplary embodiment of an X-ray tube.

FIG. 11 schematically illustrates a view-direction 92 of a so-to-speak central beam, and a plurality of view-directions 95 for beams along the movement path.

According to a further example, the "inclination of the focal track" relates to an inclination in relation to the viewing direction. For example, the inclination degree is decreasing in the viewing direction.

Figure 12:
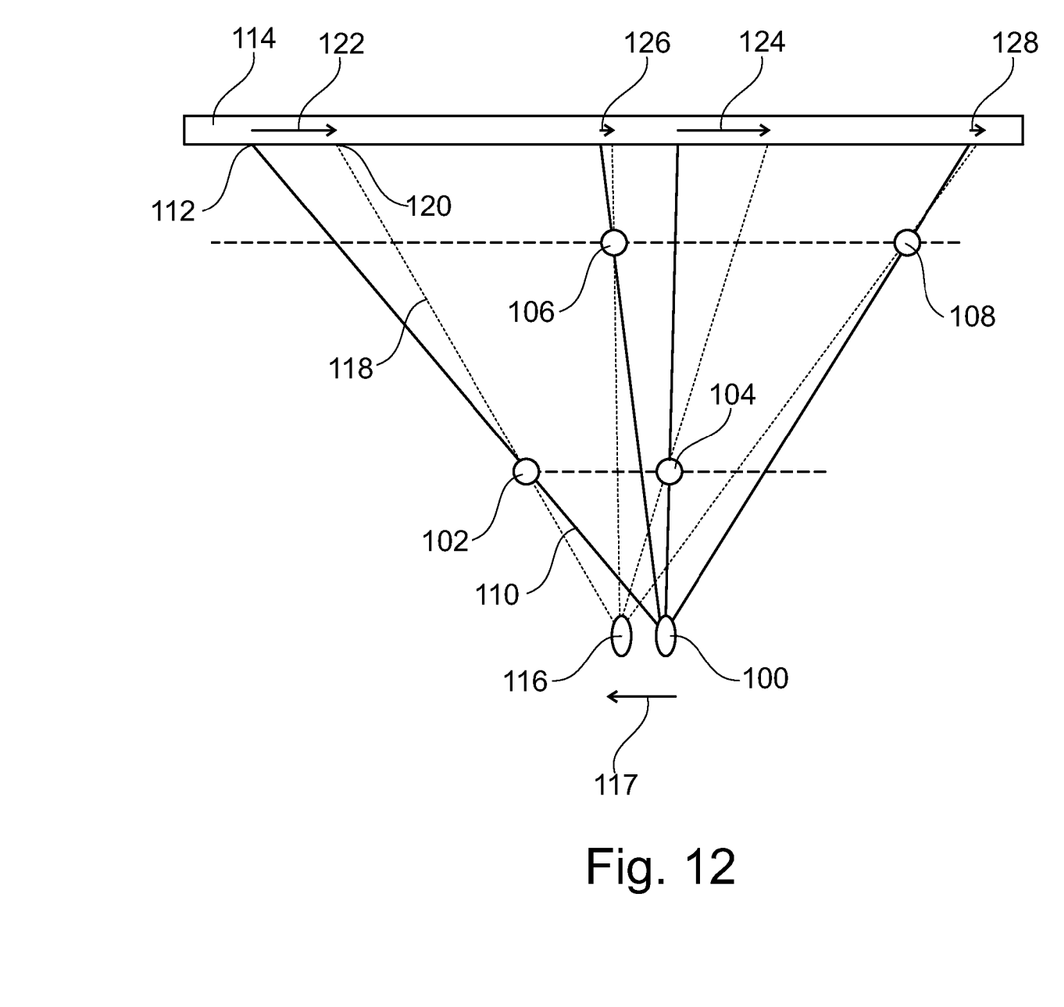
FIG. 12 shows a further exemplary embodiment of an X-ray tube in combination with a detector according to an exemplary embodiment of the present invention.

FIG. 12 schematically shows the concept of a moving X-ray focal spot. A first focal spot position 100 and the resulting projections are shown, respectively projection points of a number of features 102, 104, 106, and 108, distributed in a spatial manner, for example detected objects inside a patient. Therefore, a plurality of connecting lines 110 are indicated starting from the first focal spot location 100, passing the respective object 102, etc., and indicating a certain position 112 on a schematically indicated X-ray detector 114.

By moving the focal spot from the first position 100 to a second position 116, which movement is indicated with movement arrow 117, the connecting lines between the focal spot and the respective objects 102, etc. would be slightly pivoted around the respective object's location. These connection lines are shown with a dotted line and are indicated with reference numeral 118. As can be seen, this would lead to a further shifted position 120 on the detector 114. The shifting vector is indicated with a respective arrow 122 for the first object 102, a second arrow 124 for the second object 104, a third arrow 126 for the third object 106, and a fourth arrow 128 for the fourth object 108. Thus, the X-ray projections of objects or points close to the detector 114 are close to each other, even though the X-ray focal spot has moved from the first position 100 to the second position 116. For object points far from the detector, i.e. closer to the X-ray source, the respective X-ray projections on the detector 114 are more distant from each other.

In the so-called default case, where the detector is close to the physician, objects closer to the physician would appear with smaller motion trajectory. Of course, in a vice versa arrangement, the respective result would also be vice versa. Thus, in case the X-ray source is arranged towards the physician and the X-ray detector is arranged away from the physician, this results in that the farther away an object from the physician, the smaller the motion trajectory of the object. Thus, moving the X-ray focal spot gives live depth information by the movement size of the various objects. The spot movement can be done in all directions, or gradually by intermediate acquisitions during the spot movement. Of course, also toggling can be provided.

By providing a moving focal spot, the user can retrieve spatial information of the presented live image although the images shown are not real stereoscopic images, i.e. they are not a left and a right image acquired from two different focal spots at the same time and provided to the user in the same time. Thus, although the images are provided as 2D images according to the present invention, the spatial information is nevertheless visible for the user by providing a sequence of images along a moving path with a moving focal spot. The different distances of features shown in one image result in different offsets or movements in the next image, when the focal spot has been moved. In this way, the user is provided with depth information about the object under examination.

Figure 13:
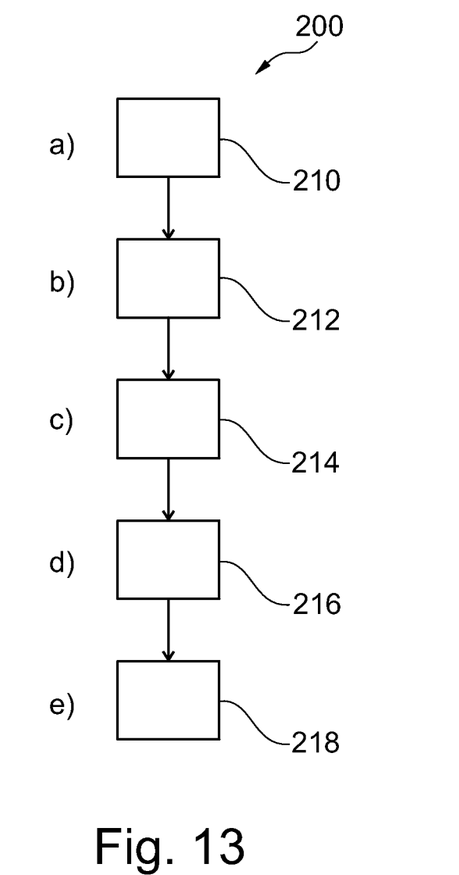
FIG. 13 shows method steps of an example of a method for providing spatial live viewing of an object according to the present invention.

FIG. 13 shows a method 200 for providing spatial live viewing of an object, comprising the following steps: In a first step 210, an electron beam is generated from a cathode arrangement towards a target area of an anode and the electron beam is controlled, for example deflected, such that the electron beam hits the anode at a moving focal spot. The electron beam is controlled, e.g. deflected, such that the focal spot moves at least in a first moving direction transverse to a viewing direction. In a second step 212, X-ray radiation is generated by the electron beam impinging on the moving focal spot. In a third step 214, X-ray radiation at least partially passing an object is detected and respective X-ray detection signals are generated. In a fourth step 216, monoscopic 2D images are generated based on the detection signals, which monoscopic 2D images relate to different view-points as defined by the moving focal spot. In a fifth step 218, the monoscopic X-ray images from the different view-points are displayed.

The first step 210 is also referred to as step a), the second step 212 as step b), the third step 214 as step c), the fourth step 216 as step d), and the fifth step 218 as step e).

For example, the changing image data comprises gradually changing image content.

According to a further example, in step e), live image data of the object is continuously shown for the moving view-points providing spatial impression about the object.

Figure 14:
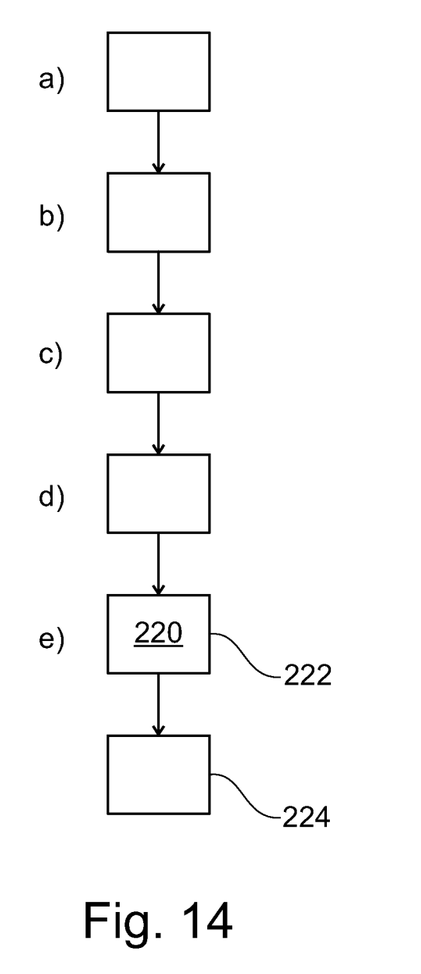
FIG. 14 shows a further exemplary embodiment of a method according to the present invention.

A shown in FIG. 14, for the displaying, a moving average 220 of several images from different moving focal spots is computed in a first sub-step 222, wherein the moving average is provided for a determined period of time. Next, in a second sub-step 224, the computed average is displayed. Thus, different blurring is provided for different depths of the object, thus providing spatial information to the user.

According to a further example (not shown), in step b), the focal spot is moved along a loop-like movement path.

According to another example (also not shown), the X-ray detector is placed below the patient and the X-ray tube is placed above the patient. This way, the X-ray images look like resulting from head movements of the physician. Using sufficient region of interest imaging, the X-ray scatter can be limited in this configuration.

2D images give clear information about x and y position of an object. But the z (depth) position is ambiguous. X-ray images are absorption images: depth clues like occlusion are missing. Presenting images from variable view-points gives the physician depth information/sensation by the relative movement size (or amount of blurring) of the displayed object of interest with respect to other displayed objects (parts).

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray tube for viewing of an object, comprising:
   a cathode arrangement;
   an anode; and
   a controller configured to control the cathode arrangement and the anode to generate an electron beam from the cathode arrangement towards a target area of the anode to generate X-ray radiation by electrons impinging on the target area,
   wherein the controller is further configured to control the electron beam such that the electrons hit the anode at a moving focal spot and to provide a movement of the moving focal spot at least in a first moving direction transverse to a viewing direction, and wherein the anode includes a continuous inclined surface for providing different heights for positions of the moving focal spot, wherein the continuous inclined surface has a continuously changing inclination along a direction of the continuously changing inclination of the continuous inclined surface between inner and outer parts of the anode.

2. The X-ray tube according to claim 1, wherein X-ray imaging is provided with a gradually moving focal spot.

3. The X-ray tube according to claim 1, wherein the cathode arrangement comprises a single cathode, and wherein the controller comprises a deflector configured to deflect the electron beam.

4. The X-ray tube according to claim 1, wherein the cathode arrangement comprises a plurality of Carbon Nanotube emitters, wherein the Carbon Nanotube emitters are configured to provide an electron beam with a moving focal spot position, and wherein the controller is configured as a control arrangement of the Carbon Nanotube emitters.

5. An X-ray imaging system for viewing of an object, comprising:
   an X-ray source;
   an X-ray detector;
   a processing unit; and
   a display device;
   wherein the X-ray source is an X-ray tube according to claim 1;
   wherein the X-ray detector is configured to provide X-ray detection signals to the processing unit;
   wherein the processing unit is configured to generate monoscopic 2D images based on the detection signals, which monoscopic 2D images relate to different viewpoints as defined by the moving focal spot; and
   wherein the display device is a 2D display configured to show the monoscopic 2D images from the different view-points.

6. The X-ray imaging system according to claim 5, wherein the moving focal spot simulates head movement of a user.

7. The X-ray tube of claim 1, wherein the moving focal spot is moved along a loop-like movement path.

8. A method for providing viewing of an object, comprising the acts of:
   generating an electron beam from a cathode arrangement towards a target area of an anode and controlling the electron beam such that the electron beam hits the anode at a moving focal spot, wherein the electron beam is controlled such that the moving focal spot moves at least in a first moving direction transverse to a viewing direction;
   generating X-ray radiation by the electron beam impinging on the moving focal spot;
   detecting the X-ray radiation at least partially passing the object and generating X-ray detection signals;
   generating monoscopic 2D images based on the X-ray detection signals, wherein the monoscopic 2D images relate to different view-points as defined by the moving focal spot; and
   displaying the monoscopic 2D images from the different view-points,
   wherein the anode includes a continuous inclined surface for providing different heights for positions of the moving focal spot, and
   wherein the continuous inclined surface has a continuously changing inclination along a direction of the continuously changing inclination of the continuous inclined surface between inner and outer parts of the anode.

9. The method according to claim 8, wherein the displaying act includes continuously showing live image data of the object for the different view-points providing spatial impression about the object.

10. The method of claim 8, wherein the moving focal spot is moved along a loop-like movement path.

11. A method for providing viewing of an object, comprising the acts of:
    generating an electron beam from a cathode arrangement towards a target area of an anode and controlling the electron beam such that the electron beam hits the anode at a moving focal spot, wherein the electron beam is controlled such that the moving focal spot moves at least in a first moving direction transverse to a viewing direction;

generating X-ray radiation by the electron beam impinging on the moving focal spot;

detecting the X-ray radiation at least partially passing the object and generating X-ray detection signals;

generating monoscopic 2D images based on the X-ray detection signals, which monoscopic 2D images relate to different view-points as defined by the moving focal spot; and displaying the monoscopic 2D images from the different view-points, wherein for the displaying act, a moving average of several images from different moving focal spots is computed; and wherein the moving average is provided for a determined period of time.

12. The method of claim 11, wherein the moving focal spot is moved along a loop-like movement path.

13. A non-transitory computer readable medium comprising computer instructions which, when executed by a processor, configure the processor to one of perform and cause performance of the acts of for providing viewing of an object:

generating an electron beam from a cathode arrangement towards a target area of an anode and controlling the electron beam such that the electron beam hits the anode at a moving focal spot;

controlling the electron beam such that the moving focal spot moves at least in a first moving direction transverse to a viewing direction;

generating X-ray radiation by the electron beam impinging on the moving focal spot;

detecting the X-ray radiation at least partially passing the object and generating X-ray detection signals;

generating monoscopic 2D images based on the X-ray detection signals, wherein the monoscopic 2D images relate to different view-points as defined by the moving focal spot; and displaying the monoscopic 2D images from the different view-points, wherein the anode includes a continuous inclined surface for providing different heights for positions of the moving focal spot, and wherein the continuous inclined surface has a continuously changing inclination along a direction of the continuously changing inclination of the continuous inclined surface between inner and outer parts of the anode.

14. The non-transitory computer readable medium of claim 13, wherein the moving focal spot is moved along a loop-like movement path.

15. An X-ray imaging system for viewing of an object, comprising:

an X-ray source having an anode, the X-ray source being configured to generate X-ray radiation towards the object by controlling an electron beam such that the electron beam hits the anode at a moving focal spot;

an X-ray detector configured to detector the X-ray radiation and generate X-ray detection signals;

a processor; and a display;

wherein the processor is configured to control the display for generating monoscopic 2D images based on the X-ray detection signals, wherein the monoscopic 2D images relate to different view-points as defined by the moving focal spot and for displaying the monoscopic 2D images from the different view-points, and wherein for the displaying of the monoscopic 2D images, a moving average of several images from different moving focal spots is computed.

16. The X-ray imaging system of claim 15, wherein the anode includes an inclined surface for providing different heights for positions of the moving focal spot.

17. The X-ray imaging system of claim 15, wherein the moving focal spot is moved along a loop-like movement path.

* * * * *